United States Patent [19]

Singh et al.

[11] Patent Number: 4,626,243

[45] Date of Patent: Dec. 2, 1986

[54] GRAVITY-INDEPENDENT INFUSION SYSTEM

[75] Inventors: Param I. Singh, Lexington; David C. de Sieyes, Wenham, both of Mass.

[73] Assignee: Applied Biomedical Corporation, Danvers, Mass.

[21] Appl. No.: 749,470

[22] Filed: Jun. 21, 1985

[51] Int. Cl.⁴ ............................................. A61M 5/00
[52] U.S. Cl. .................................. 604/141; 604/246; 138/44
[58] Field of Search ....................... 604/131, 140–148, 604/246; 138/40, 44, 45; 222/95, 96, 105

[56] References Cited

U.S. PATENT DOCUMENTS

| | | |
|---|---|---|
| 2,319,498 | 5/1943 | Gerard .............................. 138/45 X |
| 2,752,951 | 7/1956 | Silverstein ............................ 138/45 |
| 3,298,367 | 1/1967 | Bergman ............................ 604/246 |
| 3,469,578 | 9/1969 | Bierman ......................... 604/246 X |
| 3,517,700 | 6/1970 | Williams et al. ...................... 138/44 |
| 3,640,277 | 2/1972 | Adelberg ........................... 604/141 |
| 3,850,348 | 11/1974 | Bessot et al. .................... 604/141 X |

*Primary Examiner*—Dalton L. Truluck
*Attorney, Agent, or Firm*—Gurdon R. Abell

[57] ABSTRACT

An infusion system utilizing a pressurized source of infusate comprises a capillary tube flow restrictor having sufficient length and suitably large ratio of length to internal diameter to provide reliably repeatable fluid resistance and minimum damage to infusate. The internal diameter of the flow restrictor may be made to decrease with increasing temperature so that the flow rate of the infusate is substantially independent of temperature. The flow restrictor may include means for indicating pressures and flow of infusate.

19 Claims, 4 Drawing Figures

GRAVITY-INDEPENDENT INFUSION SYSTEM

BACKGROUND OF THE INVENTION

1. Field of the Invention

This invention relates to infusion apparatus and more particularly to apparatus for infusing, into a living patient, a desired amount of infusate substantially independently of gravitational forces or temperature changes.

2. Prior Art Problem

Intravaneous (IV) infusion of fluids is one of the most widespread and lifesaving procedures in medicine. However, the use of present IV infusion systems is plagued by one or more of three limitations: first, standard IV sets that depend upon gravity for powering fluid flow are critically dependent upon elevation level of the infusate and are too tall for many necessary sites such as ambulances and battlefields; second, IV sets that utilize pumps or drop-counting electronics tend to be both expensive and operationally fragile; and third, IV sets which employ a tubing clamp to control the flow from a pressurized source of infusate are difficult to adjust and may not reliably maintain a desired rate of flow. And, superimposed upon these limitations is the tendency of temperature changes to upset flow settings.

SUMMARY OF THE INVENTION

It is accordingly the principal object of this invention to provide an infusion system, of the class described, which provides reliably predictable flow of infusate independently of elevation of infusate and without damage to infusate. It is a further object of this invention to provide a flow of infusate which is substantially independent of temperature. According to this invention, the desired objects are attained by an infusion system utilizing a pressurized source of infusate of known and controllable pressure which drives a known flow through a fixed selectable fluid resistance comprising a capillary flow restrictor having a sufficient length and suitably large ratio of length to internal diameter to provide reliably repeatable fluid resistance with minimum damage to infusate. Flow through the fluid resistance may be made substantially independent of temperature by causing the internal diameter of the flow restrictor to decrease as temperature increases. Other objects of this invention, as well as means for attaining them, are set forth in the accompanying Specification and Drawings, wherein:

DESCRIPTION OF THE INVENTION

Figure 1:
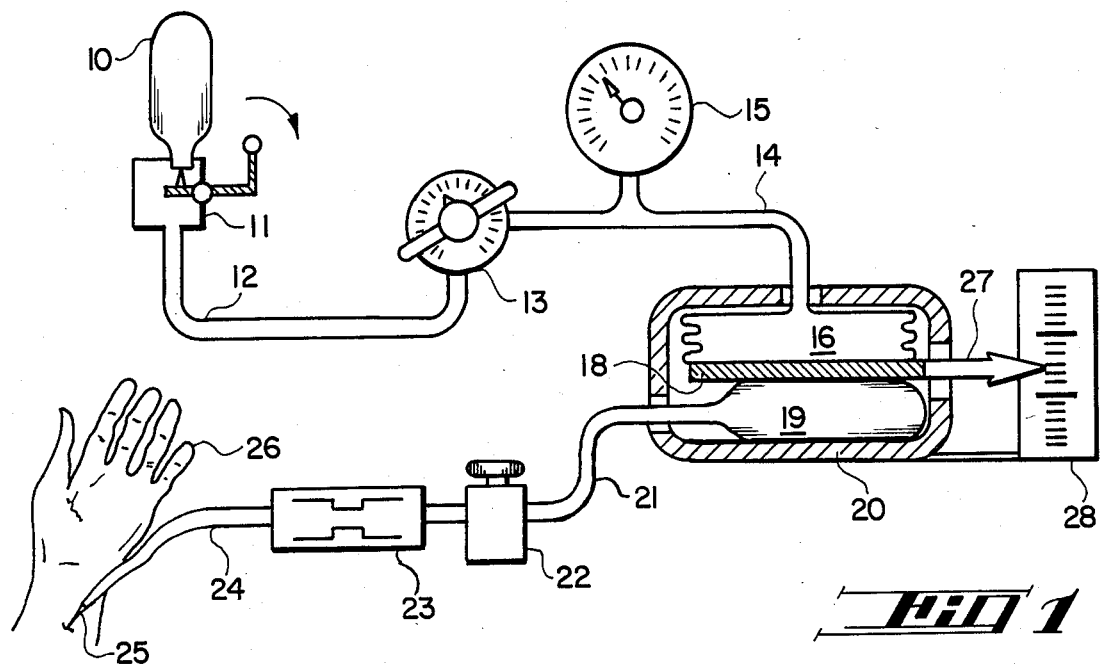
FIG. 1 is a schematic block diagram of an infusion system according to this invention.

Reference is made to FIG. 1, which is a schematic block diagram of an infusion system according to this invention. The system comprises a source of pressurized gas which may typically be a standard small carbon dioxide cartridge 10 which can be opened by actuator 11; this combination is frequently provided to inflate life vests and the like. Carbon dioxide gas at a pressure of 800–1100 psi flows through tubing 12 to adjustable pressure regulator 13 where the pressure is reduced to a driving pressure in the range of 200–500 Torr (4–10 psi). Pressure gauge 15 verifies the pressure of this gas which is then carried by tubing 14 to an inflatable gas bladder 16 which presses upon a septum 18 which in turn presses upon an infusate bag 19 which contains the liquid to be infused - physiologic saline, blood plasma, citrated whole blood, or the like. Gas bladder 16, septum 18 and infusate bag 19 are snugly housed in rigid case 20, so that the liquid pressure in infusate bag 19 equals the driving pressure in tubing 14. The infusate liquid flows through flexible tubing 21 through a tubing clamp 22 which can be manipulated to allow or cut off flow, and then flows through a flow restrictor 23 which provides a high and constant resistance to flow. The liquid then flows through flexible tube 24 and hypodermic needle 25 to the patient, indicated by 26. To monitor the progress of the infusion, and the amount of infusate remaining, septum 18 is provided with pointer 27 and scale 28.

Since the gas driving pressure is considerably greater than changes in hydrostatic pressure of the order of 0.5 psi, due to changes of the order of one foot in the relative altitudes of the infusate bag and the patient, flow rates in this infusion system are substantially independent of gravity forces.

If flow restrictor 23 exhibits a constant known resistance to flow of infusate, the rate of flow may be ascertained by noting the setting of pressure regulator 13 or the indication of pressure gauge 15, in the context of that resistance. Therefore, the regulator and pressure gauge may conveniently be calibrated in terms of flow, rather than merely in terms of pressure.

Figure 2:
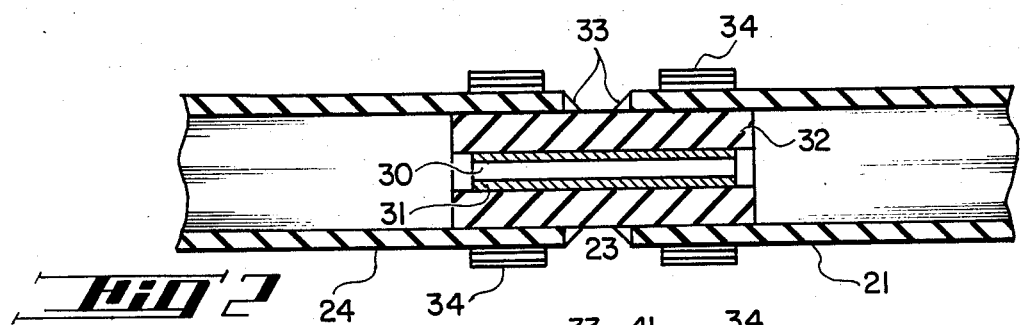
FIG. 2 is a longitudinal cross-section of a simple flow restrictor which may be used with this system.

Reference is now made to FIG. 2, which is a longitudinal cross-section of a simple flow restrictor, according to this invention, which can exhibit the requisite flow characteristics. Flow restrictor 23 comprises a small-bore flow passage 30 defined by a length 31 of hypodermic needle tubing snugly held in a longer length 32 of elastomeric tubing. Flexible tubes 21 and 24 are slipped over the ends of tubing 32. These components are joined together by tight wrappings 34, and the joint between tubing 32 and flexible tubes 21 and 24 may be reinforced by some applied adhesive 33. Typically, flow passage 30 may be one to several centimeters in length, with a bore of the order of a few tenths of a millimeter. It is to be understood that, in the Figures, it is necessary to exaggerate dimensions, such as tubing bore and thickness, in the interest of ease of comprehension.

In order that flow restrictor 23 may exhibit a constant and linear known resistance, it is required that the flow be laminar and that the length-diameter ratio of the flow passage 30 be sufficient. And, to protect the formed elements of blood used as an infusate, it is necessary that fluid shear forces not be excessive. These requirements can be met if the length-diameter ratio of flow passage 30 is at least 10, if the flow Reynolds number is well below 2000 and, if the infusate is blood, if shear rate is less than $10^5$ sec$^{-1}$. The Reynolds Number criterion is easily met for all structures of interest. The shear rate criterion is met if the length, in centimeters, is at least 0.0012 times the product of the driving pressure, in Torr, times the cube root of the flow rate, in milliliters per hour. Experience shows that these criteria may be met, for infusion flow rates of interest, by flow passage diameters of a few tenths of a millimeter and lengths of three millimeters or more for aqueous infusates or a few centimeters for blood, with driving pressure of 500 Torr or less, the recommended pressure limit for many infusate bags. In practice, flow passage length may be varied to compensate for variation of internal diameter among different lots of hypodermic needle tubing, a length reduction of 4N percent compensating for a diameter reduction of N percent. Longer flow passage lengths facilitate such trimming.

Typical infusates, being largely water, exhibit a fluid viscosity which decreases as temperature increases, roughly at the rate of 2% viscosity change per degree Celsius. While this viscosity change, and the consequent change in flow rate, can be compensated by suitable scaling or interpretation of the pressure settings or measurements, it would be convenient to use a flow restrictor having a fluid resistance which varies with temperature in a compensating manner.

Figure 3:
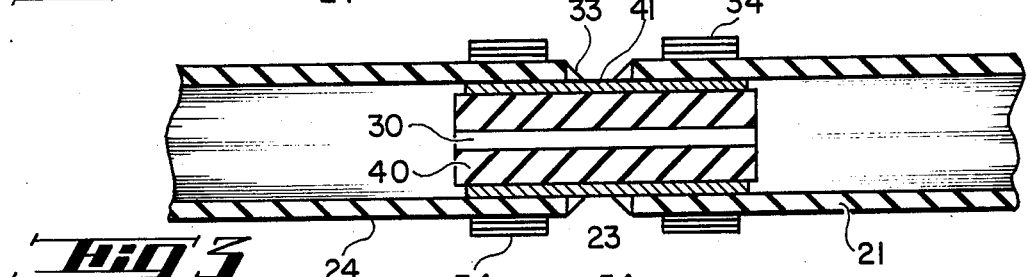
FIG. 3 is a longitudinal cross-section of a temperature compensating flow restrictor which controls a flow rate which may be substantially independent of temperature.

Reference is now made to FIG. 3, which is a longitudinal cross-section of a flow restrictor which can exhibit flow resistance which varies with temperature in such a way that flow is substantially independent of changes in temperature. Flow passage 30 is defined by the inner diameter of a thick-walled elastomeric tube 40, the outer diameter of which fits snugly in a surrounding metallic tube 41. Flexible tubes 21 and 24 are slipped over the ends of tube 40 and, again, the components are joined together by tight wrappings 34, and the joint between flexible tubes 21 and 24 and metallic tube 41 may be reinforced with some applied adhesive 33.

Typical metals have thermal coefficients of linear expansion of the order of $10^{-5}$ per degree C., while those of typical elastomers are about ten times larger. Therefore, as temperature increases, elastomeric tube 40 tends to swell more than can be accommodated by the expansion of surrounding metal tube 41. Since elastomers are not very compressible, the swelling is accommodated by a decrease in the inner diameter of elastomeric tube 40, the decrease being greater for larger ratios of outer to inner diameter of tube 40. For most combinations of metal and elastomer, a ratio of 4 to 10 can yield a fluid resistance which compensates reasonably well for viscosity change over the temperature range of interest; a ratio of 6, in a typical case, could compensate within 1.5% from 18 to 42 degrees C.

Figure 4:
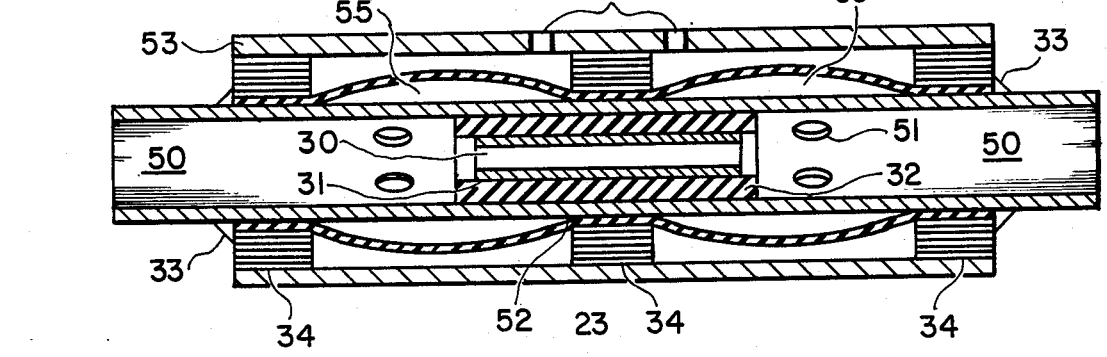
FIG. 4 is a longitudinal cross-section of a flow restrictor which incorporates means for indicating infusion pressure and flow.

Reference is now made to FIG. 4, which is a longitudinal cross-section of a flow restrictor which incorporates means for indicating infusion pressure and flow. The fluid resistance element is similar to that shown in FIG. 2, comprising a length 31 of capillary tubing defining the flow passage 30 and snugly held by a length 32 of elastomeric tubing. This assembly is snugly mounted within a long metallic tube or duct 50 which is provided with holes 51 just outside the ends of tubing 32. Surrounding duct 50 is a long thin-wall elastomeric tube 52 which is joined to duct 50 with tight wrappings 34 to form a pair of inflatable annuli 55. This assembly is then placed in a transparent cylindrical spaced-apart jacket 53 which is provided with small vent holes 54. Flexible tubes 21 and 24 may be slipped over the ends of duct 50 and fastened thereto with tight wrappings, as in the case of the restrictor assemblies shown in FIGS. 2 and 3. And the joint between thin-wall tube 52 and duct 50 may be reinforced by some applied adhesive 33.

The inner surface of transparent jacket 53 is rough or frosted, so that it appears white unless touched by the outer surface of an inflatable annulus 55, in which case it takes on the color of that surface. To exploit this fact, the upstream annulus 55, nearest flexible tube 21, is colored green on the outside, and the downstream annulus, nearest flexible tube 24, is colored red. Therefore, if flow pressure is applied, it will inflate the upstream annulus 55, and the upstream part of jacket 53 will exhibit a green band, signifying flow. But if flow is blocked downstream, as by kinking of flexible tube 24 or occlusion of the needle, pressure will rise in the downstream annulus 55 and the downstream part of jacket 53 will exhibit a red band, signifying blockage.

Given the foregoing teaching, those skilled in the art to which this invention pertains may readily devise further or extended embodiments. For one example, the restrictor assembly shown in FIG. 2, comprising a metallic tube encased in an elastomeric tube, may be replaced by a thick-walled small-bore plastic cylinder. For another example, the gas-powered pressure source shown and described with respect to FIG. 1 may be replaced by a spring-driven mechanism for squeezing infusate bag 19. Also, it is not necessary to provide a pressure gauge 15 if the setting of regulator 13 is readable and reliable. In case of a regulator malfunction which might apply excessive presure, I prefer to add a pressure-relief safety valve to tubing 14, connected to a shrill whistle to warn the operator of such an event. And, while I prefer to make the inner surface of the transparent jacket rough, and to color the outside of the inflatable annuli, in the embodiment of FIG. 4, neither of these provisions is necessary. Various other features and advantages not specifically enumerated will occur to those versed in the art, as likewise many variations of the embodiments which have been illustrated, all of which may be achieved without departing from the spirit and scope of the invention as defined by the following claims:

I claim:

1. An infusion system comprising a source of liquid infusate contained in an infusate bag and pressurized by means external to said bag to a substantially constant known driving pressure , of at least 200 Torr, said pressure driving a flow rate of said liquid infusate through a cutoff valve in series with a flow restrictor of selectable, substantially constant, known hydraulic resistance, said flow restrictor consisting of at least one small-bore flow passage having a length and a diameter, the ratio of said length to said diameter being at least 10, and said length being at least 3 millimeters, and said restrictor providing substantially all of the resistance to flow of said liquid infusate when said cutoff valve is open and said infusate is flowing, whereby said flow rate is then substantially constant.

2. An infusion system according to claim 1, for use with bloodcontaining infusates, in which said length, in centimeters, is at least 0.0012 times the product of the driving pressure, in Torr, times the cube root of the flow rate, in milliliters per hour.

3. An infusion system according to claim 1 in which said smallbore flow passage of said flow restrictor is defined by the length and inside diameter of a length of capillary tubing.

4. An infusion system according to claim 3 in which said length of capillary tubing is composed of rigid material.

5. An infusion system according to claim 4 in which said length of rigid capillary tubing is snugly held in a length of elastomeric tubing adapted to be received within ends of flexible tubes of said infusion system, to connect to said system.

6. An infusion system according to claim 1 in which said flow restrictor exhibits hydraulic resistance increasing with temperature, said small-bore flow passage being defined by the length and inside diameter of a length of thick-wall capillary tubing of elastomeric material having a first temperature coefficient of expansion, and the outside diameter of said capillary tubing being constrained by a surrounding length of tubing of rigid material having a second, and lesser, temperature coefficient of expansion.

7. An infusion system according to claim 6 in which the ratio of said outside diameter to said inside diameter of said thick-wall capillary tubing is in the range of 4 to 10.

8. A flow restrictor, for use in an infusion system comprising a source of liquid infusate pressurized to a substantially constant known driving pressure, from 200 up to about 500 Torr, said pressure driving a flow rate of said liquid infusate through said restrictor, said restrictor consisting of at least one small-bore flow passage having a length and a diameter, the ratio of said length to said diameter being at least 10, and said length being at least 3 millimeters, said restrictor having hydraulic resistance adequate to provide a pressure differential of flowing liquid infusate of the order of 200 to 500 Torr, and said restrictor further comprising connection means for connecting said restrictor into said infusion system, said connection means being adequate to withstand driving pressure up to at least 500 Torr.

9. A flow restrictor according to claim 8, for use with blood-containing infusates, in which said length, in centimeters, is at least 0.0012 times the product of the driving pressure, in Torr, times the cube root of the flow rate, in milliliters per hour.

10. A flow restrictor according to claim 8 in which said smallbore flow passage is defined by the length and inside diameter of a length of capillary tubing.

11. A flow restrictor according to claim 10 and further capable of indicating pressures and flow of infusate, said flow restrictor further comprising: a tubular duct sealably surrounding said length of capillary tubing and extending upstream and downstream thereof; holes in the wall of said duct at locations just upstream and downstream of said capillary tubing; thin-wall elastomeric tubing surrounding said duct and sealed thereto at distances upstream and downstream of said holes to provide sealed annuli inflatable by pressurized infusate flowing outward through said holes; and a transparent cylindrical jacket surrounding said elastomeric tubing and radially spaced therefrom at a small distance such that the elastomeric tubing touches the jacket when the annuli are inflated.

12. A flow restrictor according to claim 11 in which the inside surface of said transparent cylindrical jacket bears an optically rough surface at locations adjacent said sealed annuli.

13. A flow restrictor according to claim 11 in which the outside surfaces of said sealed annuli are colored.

14. An infusion system according to claim 1 in which said known driving pressure may be as high as 500 Torr.

15. An infusion system according to claim 1 in which said means, by which said source of liquid infusate is pressurized, comprises an inexpansible case which contains said infusate bag and which also contains an inflatable gas bladder inflated by a source of gas at a substantially constant known gas pressure.

16. An infusion system according to claim 15 in which a septum is interposed between said infusate bag and said inflatable gas bladder, and said septum bears a pointer which moves with respect to a scale fixed to said inexpansible case, as said liquid infusate flows from said infusate bag.

17. A flow restrictor, for use in an infusion system comprising a source of liquid infusate pressurized to a substantially constant known driving pressure driving a flow rate of liquid infusate through said restrictor, comprising a smallbore flow passage, defined within a length of capillary tubing and having a length and a diameter, the ratio of said length to said diameter being at least 10, and said length being at least 3 millimeters, said flow restrictor being further capable of indicating pressure and flow of said liquid infusate and further comprising: a tubular duct sealably surrounding said capillary tubing and extending upstream and downstream thereof; holes in the wall of said duct at locations just upstream and downstream of said capillary tubing; thin-wall elastomeric tubing surrounding said duct and sealed thereto at distances upstream and downstream of said holes to provide sealed annuli inflatable by pressurized infusate flowing outward through said holes; and a transparent cylindrical jacket surrounding said elastomeric tubing and radially spaced therefrom at a small distance such that said elastomeric tubing touches said jacket when said annuli are inflated.

18. A flow restrictor according to claim 17 in which the inside surface of said transparent cylindrical jacket bears an optically rough surface at locations adjacent said sealed annuli.

19. A flow restrictor according to claim 17 in which the outside surfaces of said sealed annuli are colored.

* * * * *